US010695131B2

(12) United States Patent
Weber et al.

(10) Patent No.: US 10,695,131 B2
(45) Date of Patent: *Jun. 30, 2020

(54) MEDICAL IMAGING SYSTEM (71) Applicant: KONINKLIJKE PHILIPS N.V., Eindhoven (NL)

(72) Inventors: Frank Michael Weber, Eindhoven (NL); Thomas Heiko Stehle, Eindhoven (NL); Irina Wachter-Stehle, Eindhoven (NL); Jochen Peters, Eindhoven (NL); Juergen Weese, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 121 days.

This patent is subject to a terminal disclaimer.

(21) Appl. No.: 15/944,919

(22) Filed: Apr. 4, 2018

(65) Prior Publication Data

US 2018/0289424 A1    Oct. 11, 2018

Related U.S. Application Data

(63) Continuation of application No. 14/895,604, filed as application No. PCT/EP2014/061254 on May 30, 2014, now Pat. No. 9,956,046.

(30) Foreign Application Priority Data

Jun. 7, 2013 (EP) ..................................... 13170984

(51) Int. Cl.
*A61B 34/10* (2016.01)
*G06T 7/33* (2017.01)
(Continued)

(52) U.S. Cl.
CPC ............ *A61B 34/10* (2016.02); *A61B 8/0883* (2013.01); *A61B 8/12* (2013.01); *G06T 7/0016* (2013.01);
(Continued)

(58) Field of Classification Search
CPC ....... G06T 7/0016; G06T 7/174; G06T 7/251; G06T 7/33; G06T 2207/10136;
(Continued)

(56) References Cited

U.S. PATENT DOCUMENTS 7,536,041 B2    5/2009  Pekar et al.
9,202,271 B2   12/2015  Awechter-Stehle et al.
(Continued)

FOREIGN PATENT DOCUMENTS

WO    2011132131 A1    10/2011

OTHER PUBLICATIONS

Korosoglou et al. "Objective quantification of aortic valvular structures by cardiac computed tomography angiography in patients considered for transcatheter aortic valve implantation." Catheterization and Cardiovascular Interventions 81.1: 148-159., Abstract Only (Year: 2012).*

(Continued)

*Primary Examiner* — Katrina R Fujita (57) ABSTRACT

The present invention relates to a medical imaging system (10) for planning an implantation of a cardiac implant (42), comprising:
  a receiving unit (12) for receiving a plurality of three-dimensional (3D) cardiac images (14, 14') showing different conditions of a heart (32) during a cardiac cycle;
  a segmentation unit (22) for segmenting within the plurality of 3D cardiac images (14, 14') a target implant region (38) and a locally adjacent region (40) that could interfere with the cardiac implant (42);

(Continued)

a simulation unit (24) for simulating the implantation of the cardiac implant (42) within the target implant region (40) in at least two of the plurality of 3D cardiac images (14, 14');

a collision evaluation unit (26) for evaluating an overlap (46) of the simulated cardiac implant (42) with the segmented locally adjacent region (40) in at least two of the plurality of 3D cardiac images (14, 14'); and a feedback unit (28) for providing feedback information to a user concerning the evaluated overlap (46).

18 Claims, 6 Drawing Sheets

(51) Int. Cl.

| | | |
|---|---|---|
| *G06T 7/174* | (2017.01) | |
| *G06T 7/246* | (2017.01) | |
| *G06T 19/00* | (2011.01) | |
| *A61B 8/08* | (2006.01) | |
| *A61B 8/12* | (2006.01) | |
| *G06T 7/00* | (2017.01) | |

(52) U.S. Cl.
CPC ............ *G06T 7/174* (2017.01); *G06T 7/251* (2017.01); *G06T 7/33* (2017.01); *G06T 19/00* (2013.01); *A61B 2034/104* (2016.02); *A61B 2034/107* (2016.02); *G06T 2207/10136* (2013.01); *G06T 2207/30048* (2013.01); *G06T 2207/30052* (2013.01); *G06T 2207/30241* (2013.01); *G06T 2210/21* (2013.01); *G06T 2210/41* (2013.01)

(58) Field of Classification Search
CPC . G06T 2207/30048; G06T 2207/30052; G06T 2207/30241; G06T 2210/21; G06T 2210/41; G06T 19/00; A61B 8/0883; A61B 8/12; A61B 34/10; A61B 2034/104; A61B 2034/107
See application file for complete search history.

(56) References Cited

U.S. PATENT DOCUMENTS

| | | |
|---|---|---|
| 2009/0304245 A1 | 12/2009 | Egger |
| 2010/0239148 A1 | 9/2010 | Zheng et al. |
| 2011/0153286 A1 | 6/2011 | Zaeuner et al. |
| 2012/0163686 A1 | 6/2012 | Liao et al. |
| 2012/0280980 A1 | 11/2012 | Neubauer |
| 2013/0057569 A1 | 3/2013 | Liao et al. |
| 2014/0177935 A1 | 6/2014 | Nair |
| 2015/0112659 A1 | 4/2015 | Mortier |

OTHER PUBLICATIONS

Piazza et al, "Two Cases of Aneurysm of the Anterior Mitral Valve . . . " Journal of Thoracic and Cardiovascular Surgery 140(3) (2010) p. 36-38.

Wachter et al "Patient Specific Models for Planning and Guidance of Minimally Invasive . . . " MICCAI 2010, pp. 526-533 2010.

Capelli et al, "Finite Element Strategies to Satisfy Clinical and Engineering Requirements". . . Annals of Biomedical Engineering vol. 40, No. 12 Dec. 2012 p. 2663-2673.

Capelli et al "Patient Specific Simulations of Transcatheter Aortic Valve Stent Implantation" Medical & Biological Engineering and Computing, vol. 50, No. 2, p. 183-192 (2012).

Ecabert et al "Automatic Model Based Segmentation of the Heart in CT Images" IEEE Transactions on Medical Imaging vol. 27(9) pp. 1189-1291 2008.

Peters et al "Optimizing Boundary Detection via Simulated Search with Applications . . . " Medical Image Analysis 14(1) 2010, p. 70.

Wong et al "Mitral Valve Injury Late After Transcatheter Aortic . . . " The Journal of Thoracic and Cardiovascular Surgery. vol. 137, No. 6. p. 1547-1549.

Comoglio et al "Aortic Valve Replacement and Mitral Valve Repair Treatment . . . " The Journal of Thoracic and Cardiovascular Surgery vol. 138, No. 4, p. 1025-1027.

Caudron et al. "Evaluation of multislice computed tomography early after transcatheter aortic valve implantation with the Edwards SAPIEN bioprosthesis." The American journal of cardiology 108.6 (2011 ): 873-881.

Fraccaro et al. "Incidence, predictors, and outcome of conduction disorders after transcatheter self-expandable aortic valve implantation." The American journal of cardiology 107.5 (2011 ): 747-754.

Himbert et al. "Feasibility and outcomes of transcatheter aortic valve implantation in high-risk patients with stenotic bicuspid aortic valves." The American journal of cardiology 110.6 (Sep. 2012): 877-883.

Piazza et al. "Anatomy of the aortic valvar complex and its implications for transcatheter implantation of the aortic valve." Circulation: Cardiovascular Interventions 1.1 (2008): 74-81.

Schultz et al. "Three dimensional evaluation of the aortic annulus using multislice computer tomography: are manufacturer's guidelines for sizing for percutaneous aortic valve replacement helpful?." European heart journal 31.7 (2009): 849-856.

Padala Met Al: "An Engineering Review of Transcatheter Aortic Valve Technologies",Cardiovascular 1 Engineering and Technology 2010 Springer Publishing Company USA,vol. 1, No. 1, Mar. 2010 (Mar. 2010), pp. 77-87.

Jayasuriya et al: "Transcatheter Aortic Valve Implantation in Aortic Stenosis: The Role of Echocardiography"; American Journal of Echocardiography, 2011, pp. 15-27.

Votta et al: Toward Patient-Specific Simulations of Cardiac Valves: State-of-The-Art and Future Directions; Journal of Biomechanics Elsevier Science Ltd. UK, vol. 46, No. 2, Jan. 2013, pp. 217-228.

\* cited by examiner

MEDICAL IMAGING SYSTEM

The present application is a continuation of U.S. patent application Ser. No. 14/895,604 filed Dec. 3, 2015, which is the U.S. National Phase application under 35 U.S.C. § 371 of International Application No. PCT/EP2014/061254, filed May 30, 2014, which claims the benefit of EP Application Serial No. 13170984.2 filed Jun. 7, 2013. These applications are hereby incorporated by reference herein.

FIELD OF THE INVENTION

The present invention relates to a medical imaging system for planning an implantation of a cardiac implant. Furthermore, the present invention relates to a corresponding method for planning an implantation of a cardiac implant. It also relates to a computer program comprising program code means for causing a computer to carry out the steps of said method. An exemplary technical application of the present invention is the planning of a transcatheter aortic valve implantation (TAVI) for treating aortic stenosis.

BACKGROUND OF THE INVENTION

Valvular heart diseases are among the most prominent causes of heart failure and premature cardiac death. Aortic valve stenosis is a very common valvular disease. This disease is often treated by implanting an artificial aortic valve via an open cardiac surgery. This is, however, a very invasive and expensive treatment. In addition, it is considered too high risks or contraindicated for many patients.

In the last decade, techniques for minimally invasive aortic valve implantation have been developed that offer a new treatment option. An alternative method for high-risk patients that cannot undergo an open-heart surgery for aortic valve replacement is a trans-catheter aortic valve implantation (TAVI). In this technique, an artificial valve is mounted on a stent which is delivered through a catheter, either transfemoral, transsubclavian, or trans-apical, under X-ray guidance, and then expanded in-place.

Although TAVI is less invasive, its long-term outcome is unclear. A current discussion is therefore, if TAVI is also beneficial for patients with only intermediate risk for valve replacement. Because their expected lifetime is much longer, the long-term benefit of the TAVI implant must be ensured.

If the TAVI implant is placed too low, i.e. reaching too far into the left ventricular outflow tract, it can impair movement of the anterior mitral leaflet. Case reports demonstrated that contact between the implant and the mitral valve leaflet led to mitral endocarditis and leaflet aneurysms, see e.g. Piazza, N. et al.: "Two cases of aneurysm of the anterior mitral valve leaflet associated with transcatheter aortic valve endocarditis: a mere coincidence?", in Journal of Thoracic and Cardiovascular Surgery 140(3) (2010) e36-e38.

First, repetitive friction between the implant and the leaflet could damage the leaflet surface. Second, the implant could act as an endocarditis bridge that favors the spread of aortic valve endocarditis to the mitral valve. Especially, the slow tissue degeneration caused by repetitive friction might become more relevant the longer the implant is present.

Therefore, preparing and planning medical procedures like TAVI before beginning an actual operation is of utmost importance. The treatment planning should particularly make sure to avoid the above explained friction between the implant and any anatomical structure of the heart. Such medical imaging procedures are also important to guide the implantation during the surgery (in real-time), since the aortic valve anatomy is not clearly visible when using X-ray imaging.

Wächter et al.: "Patient specific models for planning and guidance of minimally invasive aortic valve implantation", MICCAI 2010, part I, LNCS 6361, pp. 526-533, 2010, Springer-Verlag Berlin Heidelberg 2010, present a method to extract the aortic valve anatomy from CT images. The therein presented method allows for detection of anatomical landmarks by exploiting the model-based segmentation. This allows to receive a fairly accurate model, in particular of the aortic valve and the coronary ostia. The method is also described in WO 2011/132131 A1, a prior patent application filed by the applicant.

Capelli, C. et al.: "Finite Element Strategies to Satisfy Clinical and Engineering Requirements in the Field of Percutaneous Valves", in Annals of Biomedical Engineering, vol. 40, No. 12, December 2012, pp. 2663-2673 discloses a study showing that beam elements are a convenient choice toward a practical and reliable clinical application of finite element modelling of percutaneous devices for valve implantation. Similar aspects are disclosed in Capelli, C. et al.: "Patient-specific simulations of transcatheter aortic valve stent implantation", in Medical & Biological Engineering & Computing, Springer, Berlin, vol. 50, no. 2, pp. 183-192.

US 2011/153286 A1 discloses a method and system for virtual percutaneous valve implantation. A patient-specific anatomical model of a heart valve is estimated based on 3D cardiac medical image data and an implant model representing a valve implant is virtually deployed into the patient-specific anatomical model of the heart valve. A library of implant models, each modeling geometrical properties of a corresponding valve implant, is maintained. The implant models maintained in the library are virtually deployed into the patient specific anatomical model of the heart valve to select an implant type and size and deployment location and orientation for percutaneous valve implantation.

However, there is still need for further improvement of such medical planning systems.

SUMMARY OF THE INVENTION

It is an object of the present invention to provide an improved medical imaging system of the kind mentioned above for planning an implantation of a cardiac implant. It is furthermore an object of the present invention to provide a corresponding method and a computer program for implementing such method.

In a first aspect of the present invention, a medical imaging system for planning an implantation of a cardiac implant is presented that comprises:

- a receiving unit for receiving a plurality of three-dimensional (3D) cardiac images showing different conditions of a heart during a cardiac cycle;
- a segmentation unit for segmenting within the plurality of 3D cardiac images a target implant region and a locally adjacent region that could interfere with the cardiac implant, wherein the target implant region is a part of a left ventricular outflow tract and the locally adjacent region is a part of a mitral valve;
- a simulation unit for simulating the implantation of the cardiac implant within the target implant region in at least two of the plurality of 3D cardiac images;

a collision evaluation unit for evaluating an overlap of the simulated cardiac implant with the segmented locally adjacent region in at least two of the plurality of 3D cardiac images; and a feedback unit for providing feedback information to a user concerning the evaluated overlap.

In a second aspect of the present invention, a medical imaging system for planning an implantation of a cardiac implant is presented that comprises:

a receiving unit for receiving a plurality of three-dimensional (3D) cardiac images showing different conditions of a heart during a cardiac cycle;

a segmentation unit for segmenting within the plurality of 3D cardiac images a target implant region and a locally adjacent region that could interfere with the cardiac implant, wherein the target implant region is a part of a right ventricular outflow tract and the locally adjacent region is a part of a tricuspid valve;

a simulation unit for simulating the implantation of the cardiac implant within the target implant region in at least two of the plurality of 3D cardiac images;

a collision evaluation unit for evaluating an overlap of the simulated cardiac implant with the segmented locally adjacent region in at least two of the plurality of 3D cardiac images; and a feedback unit for providing feedback information to a user concerning the evaluated overlap.

In a third aspect of the present invention, a method for planning an implantation of a cardiac implant is presented, which comprises the steps of receiving a plurality of three-dimensional (3D) cardiac images showing different conditions of a heart during a cardiac cycle;

segmenting within the plurality of 3D cardiac images a target implant region and a locally adjacent region that could interfere with the cardiac implant, wherein the target implant region is a part of a left ventricular outflow tract and the locally adjacent region is a part of a mitral valve;

simulating the implantation of the cardiac implant within the target implant region in at least two of the plurality of 3D cardiac images;

evaluating an overlap of the simulated cardiac implant with the segmented locally adjacent region in at least two of the plurality of 3D cardiac images; and providing feedback information to a user concerning the evaluated overlap.

In a fourth aspect of the present invention, a method for planning an implantation of a cardiac implant is presented, which comprises the steps of receiving a plurality of three-dimensional (3D) cardiac images showing different conditions of a heart during a cardiac cycle;

segmenting within the plurality of 3D cardiac images a target implant region and a locally adjacent region that could interfere with the cardiac implant, wherein the target implant region is a part of a right ventricular outflow tract and the locally adjacent region is a part of a tricuspid valve;

simulating the implantation of the cardiac implant within the target implant region in at least two of the plurality of 3D cardiac images;

evaluating an overlap of the simulated cardiac implant with the segmented locally adjacent region in at least two of the plurality of 3D cardiac images; and providing feedback information to a user concerning the evaluated overlap.

In a still further aspect of the present invention, a computer program is presented comprising program code means for causing a computer to carry out the steps of either of the above-mentioned methods when said computer program is carried out on the computer.

The idea of the invention is to automatically simulate and evaluate the position of the cardiac implant within a plurality of 3D cardiac images based on a segmentation of said images. Said cardiac images may be 3D CT or MRI images. In a preferred embodiment, 3D transesophageal echography (TEE) images acquired with an ultrasound imaging system may be used.

In contrast to most of the prior art planning systems of this kind, not only one cardiac image but a plurality of such 3D cardiac images are used for the simulation and evaluation. The term "a plurality" shall be understood in the context of the present invention as "at least two". This has a couple of advantages: First, it is tedious to check a series of images for identifying the most relevant image for planning the implantation of the cardiac implant. A doctor or a medical assistant usually has to manually find a suitable image which may be quite time-consuming. Secondly, by evaluating a plurality of 3D cardiac images showing different conditions of the heart during the cardiac cycle, possible unwanted collisions between the cardiac implant and parts of the heart that move during the cardiac cycle may be estimated in a much more precise manner. Depending on the heart movement, the cardiac implant may interfere with one heart region in a first image, but may not interfere with said region of the heart when considering it in another image. Using a plurality of 3D cardiac images for the planning procedure therefore allows to more precisely determining the implant position, the size and shape of the cardiac implant.

Preferably, the plurality of 3D cardiac images is a sequence of timely consecutive cardiac images showing one or more complete cardiac cycles. By segmenting all of these images, a dynamic segmentation is established which allows to simulate the movement of the heart. This may either be done in a pre-planning step before the actual implantation by means of cardiac images that have been pre-acquired. It may, however, also be done in real-time during the actual implantation.

A further characteristic of the presented system and method is that not only the target implant region is segmented but also a locally adjacent region of the heart that could, e.g. due to the heart movement, interfere with the cardiac implant. When using the presented system e.g. for TAVI, the target implant region is defined as the left ventricular outflow tract. Depending on the size and position of the TAVI implant it could however also interfere and overlap with the mitral valve leaflet. This mitral valve leaflet would then be considered as locally adjacent region in the meaning of the present invention, such that it will be segmented as well. Since a plurality of 3D cardiac images are used, this allows to evaluate possible overlaps of the TAVI implant with the mitral valve leaflet for different positions of the leaflet during the cardiac cycle. Of course, one would say that the overlap is maximum when the mitral valve is completely open. However, manually finding the image that exactly illustrates the open mitral valve is fairly difficult. Apart from that, collisions of the mitral valve with the cardiac implant may also occur in other states of the mitral valve than the fully open state.

A further characteristic of the present invention is the simulation of the cardiac implant within the target implant region. Preferably, a simple geometrical model may be used to simulate the cardiac implant. This simulated cardiac implant may be used to evaluate an overlap with the locally adjacent region that has been segmented prior thereto. A feedback unit, which may e.g. be realized by a display, then provides feedback information concerning the evaluated overlap to a physician or medical staff. The overlap may e.g. be displayed for all evaluated cardiac images. This direct feedback concerning possible collisions of the cardiac implant with parts of the heart based on a plurality of 3D cardiac images is a very powerful tool during planning of such a cardiac implantation.

According to a preferred embodiment, the simulation unit is configured to simulate the implantation of the cardiac implant within the target implant region in each of the plurality of 3D cardiac images, and the collision evaluation unit is configured to evaluate the overlap of the simulated cardiac implant with the segmented locally adjacent region in each of the plurality of 3D cardiac images.

This means that the overlap evaluation is not only performed in a subset of the received plurality of 3D cardiac images, but in all of the received 3D cardiac images. In this way, the amount of overlap data is further increased, such that the overlap evaluation is refined. The overlap data may therefore be evaluated for a whole timely consecutive imaging sequence, meaning that the overlap of the locally adjacent region (e.g. the mitral valve leaflet) with the virtual cardiac implant may be calculated time-dependent over a complete cardiac cycle.

Accordingly, the feedback unit is in this embodiment configured to provide feedback information to the user concerning the evaluated overlap in each of the plurality of 3D cardiac images. This feedback information may be displayed for each of the 3D cardiac images separately, but also in an overview for all 3D cardiac images together.

According to a further embodiment, the feedback information provided by the feedback unit includes a quantified extent of the overlap and/or a location where the overlap occurs in the 3D cardiac images. On a display, it may be exactly shown to the physician at which positions an overlap between the simulated cardiac implant and the segmented locally adjacent region occurs. Furthermore, an indicator about the extent of the overlap may be visualized. It may for example be illustrated on the display that at a given position the overlap has a given size, e.g. a few millimeters.

According to a further preferred embodiment, the collision evaluation unit is further configured to determine in each of the plurality of 3D cardiac images the overlap at a plurality of different spatial locations along a longitudinal axis along which the target implant region substantially extends. Referring back to the example of using the system for TAVI, this means that the overlap between the virtual implant and the mitral valve leaflet is calculated as a function of the implant depth. The target implant region may then be defined as prolongation of the substantially elliptical left ventricular outflow tract cross-section towards the left ventricle. A coordinate system may be used as an auxiliary means, wherein the longitudinal axis of the left ventricular outflow tract indicates the z-axis. In the above-mentioned embodiment, the collision evaluation unit may determine in each of the plurality of 3D cardiac images the overlap along the z-axis, or in other words, as a function of the z-position.

In a preferred embodiment, the collision evaluation unit is further configured to determine for each of the plurality of different spatial locations a maximum overlap by comparing the overlaps in the 3D cardiac images at the respective spatial locations with each other.

In other words, the overlaps evaluated in each of the images may be compared with each other, depending on the position on the z-axis. For each position on the z-axis, one of the plurality of 3D cardiac images is selected in which the most prominent or largest overlap is detected. The result may be a motion analysis of the examined region of the heart that, for example, shows for every or a plurality of positions within the left ventricular outflow tract a maximum overlap of the virtually simulated cardiac implant with the mitral valve leaflet over the whole cardiac cycle.

In a further preferred embodiment, the feedback unit is configured to provide a graphical representation illustrating the maximum overlaps as a function of the different spatial locations along the longitudinal axis z.

This graphical representation may be e.g. a graph that shows the maximum overlap on the axis of ordinates in dependency of the position on the longitudinal axis shown along the axis of abscissae. Since the maximum overlap at each position on the longitudinal axis of the target implant region has been found by comparing the overlaps at the respective position in each of the 3D cardiac images, such a graph shows an aggregated overlap information taken from all received 3D cardiac images. The term "maximum overlap" therefore indicates a relative maximum at the respective spatial position, i.e. the highest received overlap value at this spatial position when comparing the received 3D cardiac images with each other at said position.

Referring back to the TAVI example, it has been shown that these location-dependent maximum overlaps between the anterior mitral leaflet movement and the prolongation of the left ventricular outflow tract vary considerably between different patients. Such an aggregated maximum overlap evaluation could therefore be a good indicator for risk of friction between the mitral valve leaflet and the TAVI implant. It has also been shown that for some patients the absolute maximum overlap (maximum overlap value of all found relative maxima) occurs closer to the aortic valve than for others. The above-mentioned graphical representation may therefore help a physician to identify patient-individual risk zones.

In a further embodiment of the present invention, the segmentation unit is configured to simulate the cardiac implant by means of a virtual model having an elliptical cross-section, wherein a normal to the elliptical cross-section coincides with a longitudinal axis along which the target implant region substantially extends.

In case of the above-mentioned TAVI example, an elliptical cross-section is a good approximation for a cross-section of a stent that is to be implanted into the left ventricular outflow tract. The shape or the outer contours of the virtual cardiac implant may therefore be simulated as the prolongation of the elliptical left ventricular outflow tract cross-section towards the left ventricle. The overlap of the mitral valve leaflet may then be calculated by mathematically determining the intersections between the segmented trajectories of the mitral valve leaflet and the elliptical tube model. In order to determine all positions where the mitral valve leaflet extends into the left ventricular outflow tract and its linear prolongation towards the left ventricle, the virtual cardiac implant model may have an infinite length.

According to a further embodiment, the system may additionally comprise an input interface that allows a user to vary a size, a shape and/or a position of the simulated cardiac implant.

The overlaps may then be evaluated for different sizes, shapes and positions of the virtual implant to automatically find the best type of implant and the best target implant position. Instead of using simplified models of the implants as mentioned above, also more sophisticated models may be used that resemble the shape and size of the implant in a more realistic way.

According to a further preferred embodiment, the segmentation unit is configured to segment the target implant region and the locally adjacent region based on a model-based segmentation.

The model-based segmentation may, for example, be conducted in a similar manner as this is described for a model-based segmentation of CT images in Ecabert, O. et al. "Automatic model-based segmentation of the heart in CT images", IEEE Transactions on Medical Imaging, Vol. 27(9), pp. 1189-1291, 2008, which is herein incorporated by reference. This model-based segmentation makes use of a geometrical mesh model of the anatomical structures of the heart and may comprise respective segments representing respective anatomic features of the heart. Such a model-based segmentation usually starts with the identification of the position and orientation of the heart within the 3D image data. This may, for example, be done using a 3D implementation of the Generalized Hough Transform. Pose misalignment may be corrected by matching the geometrical mesh model to the image, making use of a global similarity transformation. The segmentation comprises an initial model that roughly represents the shape of the anatomical features of the heart. Said model may be a multi-compartment mesh model with triangular meshes. This initial model will be deformed by a transformation. This transformation is decomposed in two transformations of different kinds: a global transformation that can translate, rotate or rescale the initial shape of the geometrical model, if needed, and a local deformation that will actually deform the geometrical model so that it matches more precisely to the anatomical object of interest. This is usually done by defining the normal vectors of the surface of the geometrical model to match the image gradient; that is to say, the segmentation will look in the received 3D imaging data for bright-to-dark edges (or dark-to-bright), which usually represent the tissue borders in the images, i.e. the boundaries of the anatomical features of the heart. Further details how this model-based segmentation may be adapted to the purposes of the herein used dynamic segmentation of moving images (e.g. 4D TEE images) will be explained further below with reference to the drawings.

In the foregoing description it was mainly referred to the different embodiments of the claimed medical imaging system. It shall be understood that the claimed method has similar and/or identical preferred embodiments as the claimed medical imaging system and as defined in the dependent claims.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
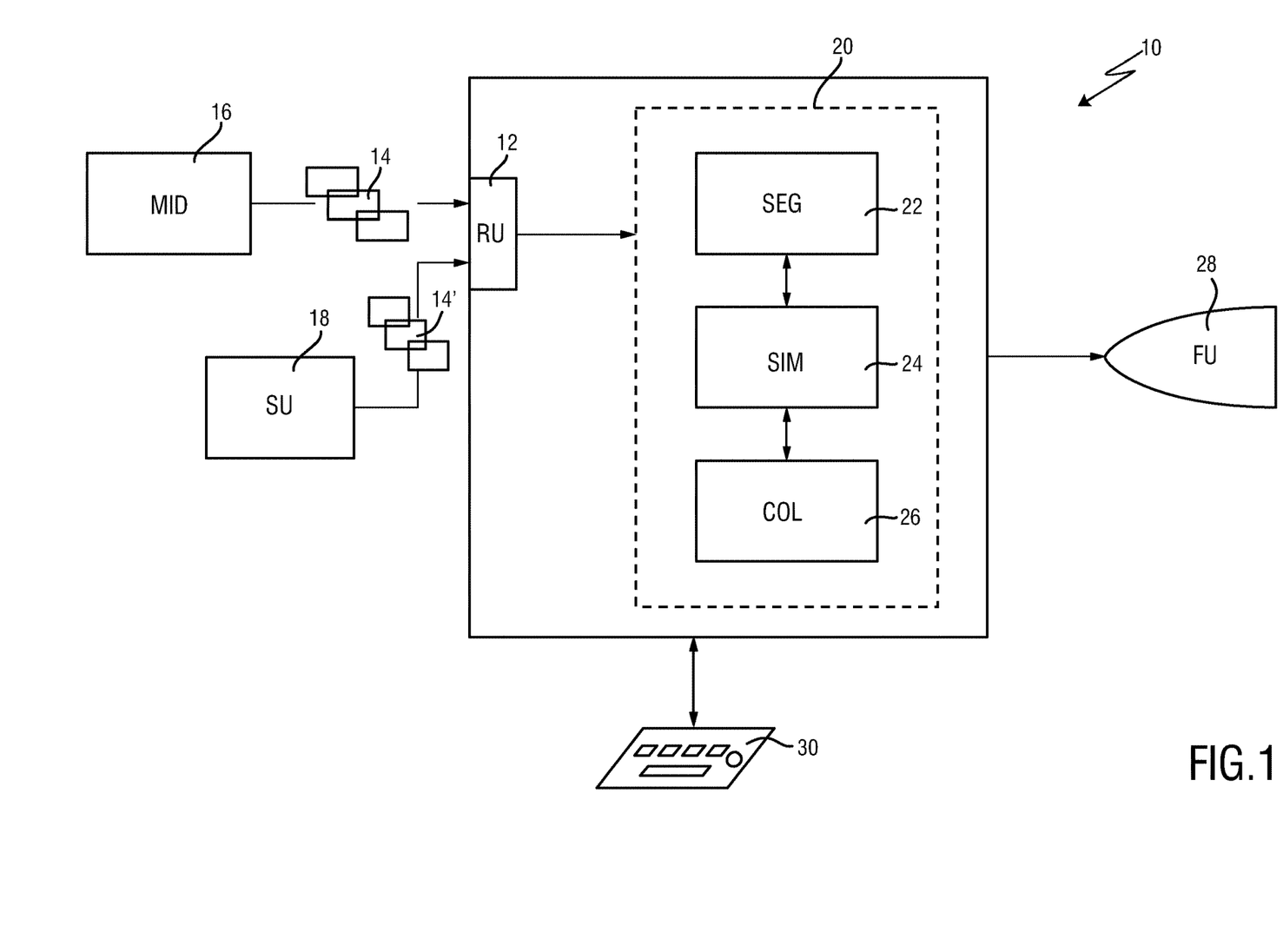
FIG. 1 shows a schematic block diagram of an embodiment of the medical imaging system according to the present invention.

FIG. 1 shows a simplified and schematic block diagram to illustrate the principal components of the presented medical imaging system, which may be particularly used for planning an implantation of a cardiac implant. The medical imaging system is therein in its entirety denoted with reference numeral 10.

It comprises a receiving unit (RU) 12 which is configured to receive a plurality of 3D cardiac images 14. Said plurality of 3D cardiac images 14 is preferably a sequence of timely consecutive frames that are acquired with a medical imaging device (MID) 16. This medical imaging device 16 may be a volumetric CT scanner, an MRI scanner or a 3D ultrasound system. A particular example of a 3D ultrasound system which may be applied for the system of the current invention is the iE33 ultrasound system sold by the applicant, in particular together with an X7-2 t TEE transducer of the applicant or another 3D transducer using the xMatrix technology of the applicant. Even though the present invention is not limited to ultrasound imaging, the following exemplary embodiments will be described with reference to the preferably used 4D TEE ultrasound imaging technique (i.e. time-dependent 3D TEE images).

It is to be noted that the medical imaging device 16 does not necessarily need to be a part of the medical imaging system 10 according to the present invention. Instead of having the 3D cardiac images 14 directly (in real time) provided by a medical imaging device 16, inspected and analyzed 3D cardiac images 14' may also be provided by a storage unit (SU) 18. The storage unit 18 may, for example, be an external or internal storage device like a hard drive on which 3D cardiac images 14' are stored which have been acquired in advance by a medical imaging device 16 or any other imaging modality.

The receiving unit 12 may be an interface (either internal or external interface) that receives the 3D cardiac images 14, 14' and transfers them to a processing unit 20. This processing unit 20 may be implemented as a CPU or a microprocessor within the medical imaging system 10. It may, for example, be a part of a personal computer that has software stored thereon that is programmed to carry out the below explained method according to the present invention.

The processing unit 20 preferably comprises a segmentation unit (SEG) 22, a simulation unit (SIM) 24 and a collision evaluation unit (COL) 26. The segmentation unit 22, the simulation unit 24 and the collision evaluation unit 26 may all either be realized as separate elements or integrated in one common processing element. All of these units 22, 24, 26 may either be hardware or software implemented.

The segmentation unit 22 is configured to segment the plurality of the 3D cardiac images 14, 14'. In case of a 4D TEE sequence, each frame is segmented. The simulation unit 24 is configured to simulate a model of a cardiac implant as well as to simulate the implantation of the cardiac implant in the 3D cardiac images 14, 14'. The collision evaluation unit 26 then evaluates an overlap of the simulated cardiac implant with anatomical features that have been segmented in the 3D cardiac images 14, 14'. The results of this evaluation may be finally shown to a user (e.g. a physician) by means of a feedback unit (FU) 28 that could be realized as a display or a screen.

Preferably, the medical imaging system 10 further comprises an input interface 30 that allows a user to steer the device 10 as well as to change the parameters that are used within the image evaluation performed by any of the units 22, 24, 26. The input interface 30 may comprise keys or a keyboard and further inputting devices, for example a trackball or a mouse. The input interface 30 is preferably connected either hardwired or wireless to the processing unit 20.

Figure 2:
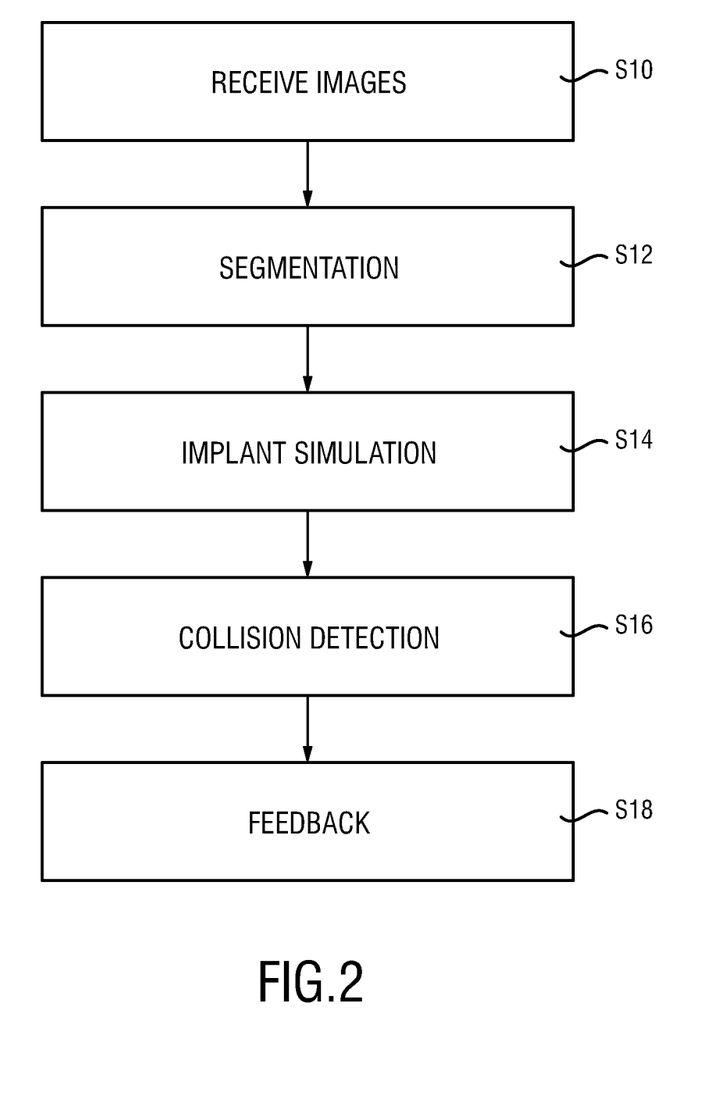
FIG. 2 shows a simplified flow diagram to illustrate an embodiment of the method according to the present invention.

FIG. 2 shows a simplified flow diagram of the method according to the present invention that is performed by the medical imaging system 10. In the following, the details of this method shall be described by means of an exemplary transcatheter aortic valve implementation (TAVI) planning procedure, wherein reference is additionally made to FIGS. 3 to 8.

1. First Method Step S10 ("Receive Images")

In the first method step, a plurality of 3D cardiac images 14, 14' are received by the system 10, wherein these cardiac images 14, 14' show different conditions of a heart 32, preferably of a human heart 32, during a cardiac cycle. In a preferred embodiment, these cardiac images 14, 14' include a sequence of 3D TEE images over time (also denoted as a 4D TEE image sequence). This 4D TEE sequence preferably shows the heart movement during a complete cardiac cycle. The image sequence may also illustrate only parts of a cardiac cycle or more than one cardiac cycle. This 4D TEE image sequence may be used to analyze the heart movement, in particular to analyze the mitral valve motion for TAVI planning.

2. Second Method Step S12 ("Segmentation")

In the next step, each frame of the received 4D TEE image sequence is segmented. This is preferably made by a model-based segmentation of the valve apparatus of the heart 32 which is performed by the segmentation unit 22.

During this step, the anatomical features of interest are segmented in order to being able to simulate the movement of these anatomical features over time. Anatomical features that are of particular interest in a TAVI are the aortic valve, the left ventricular outflow tract, into which the cardiac implant is inserted, as well as the anterior mitral leaflet, since, depending on the position and size of the cardiac implant, the anterior mitral leaflet may collide with the medical implant during its natural movement.

Figure 3:
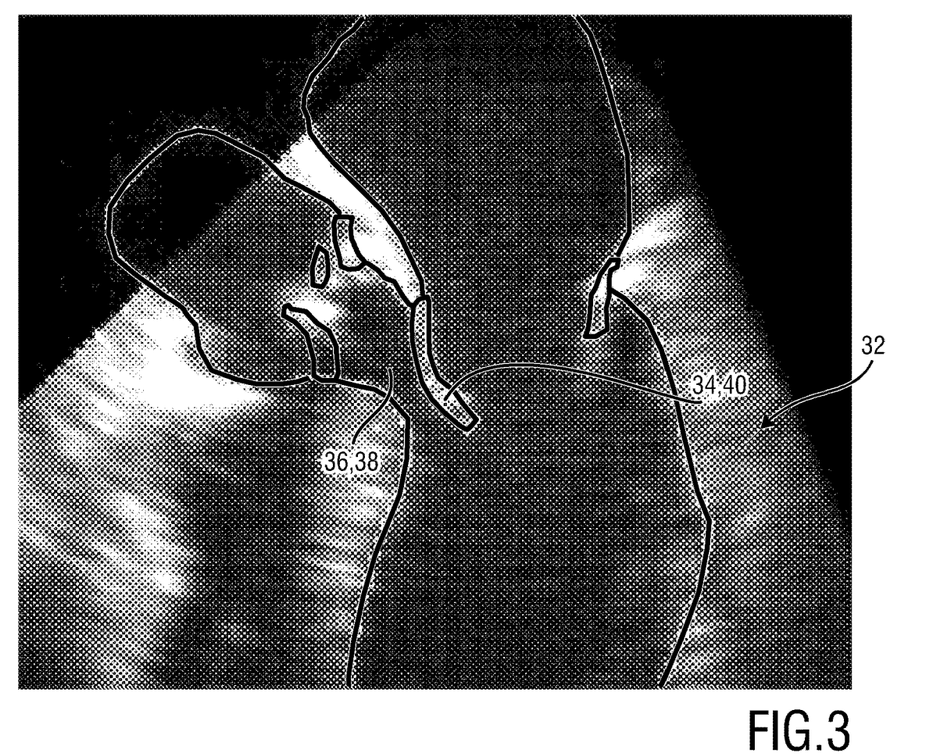
FIG. 3 shows an exemplary cardiac image that has been segmented according to the method of the present invention.
Figure 4:
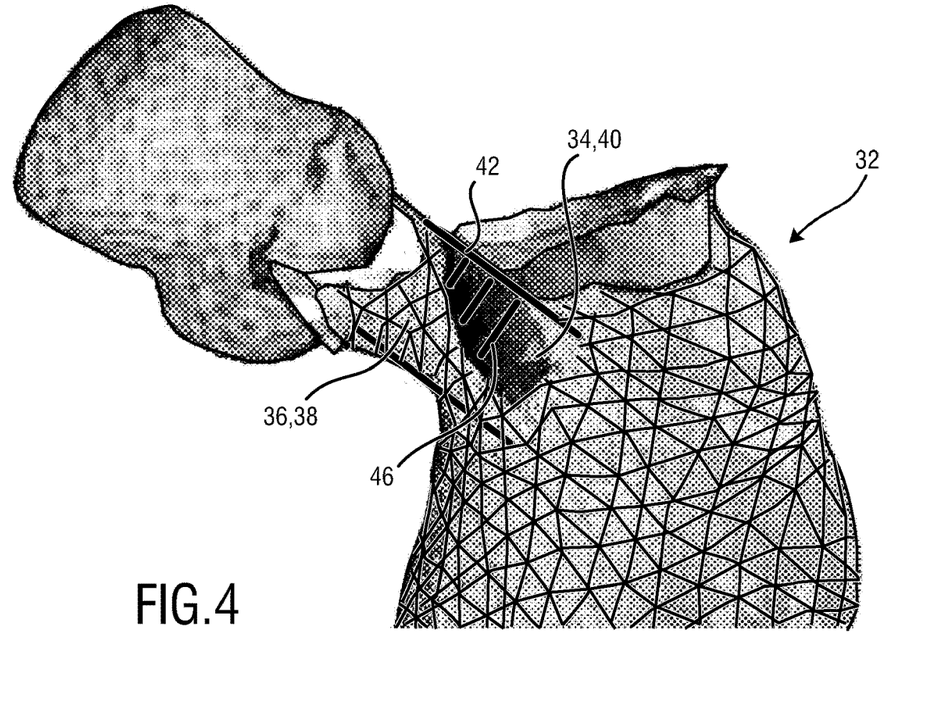
FIG. 4 schematically illustrates the results of the segmentation and collision detection according to the present invention.
Figure 5:
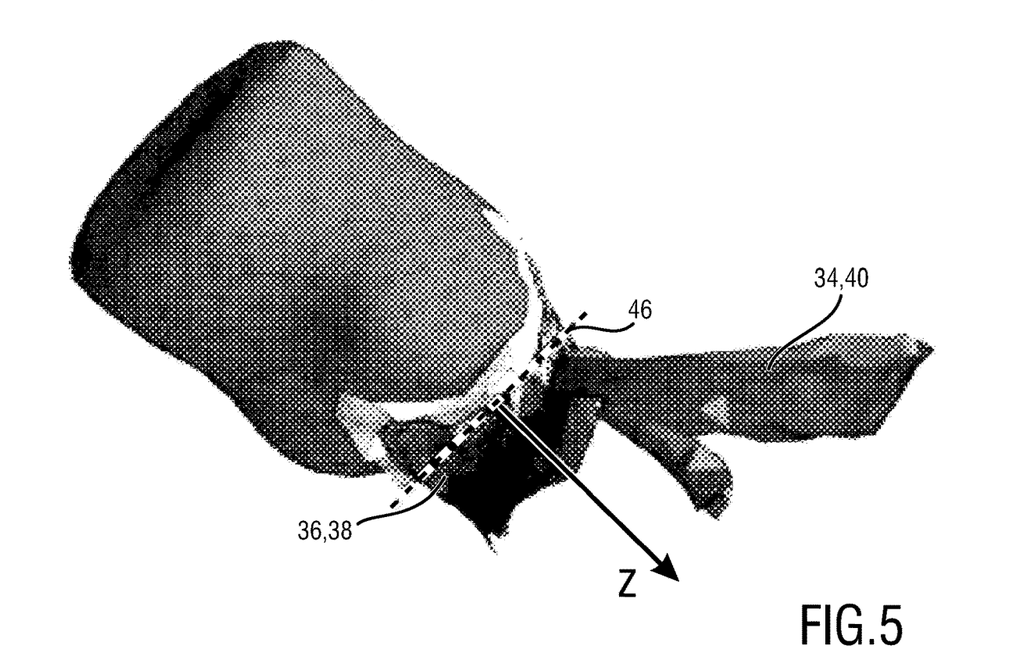
FIG. 5 shows a further model of the heart that may result from the segmentation performed by the presented system.
Figure 6:
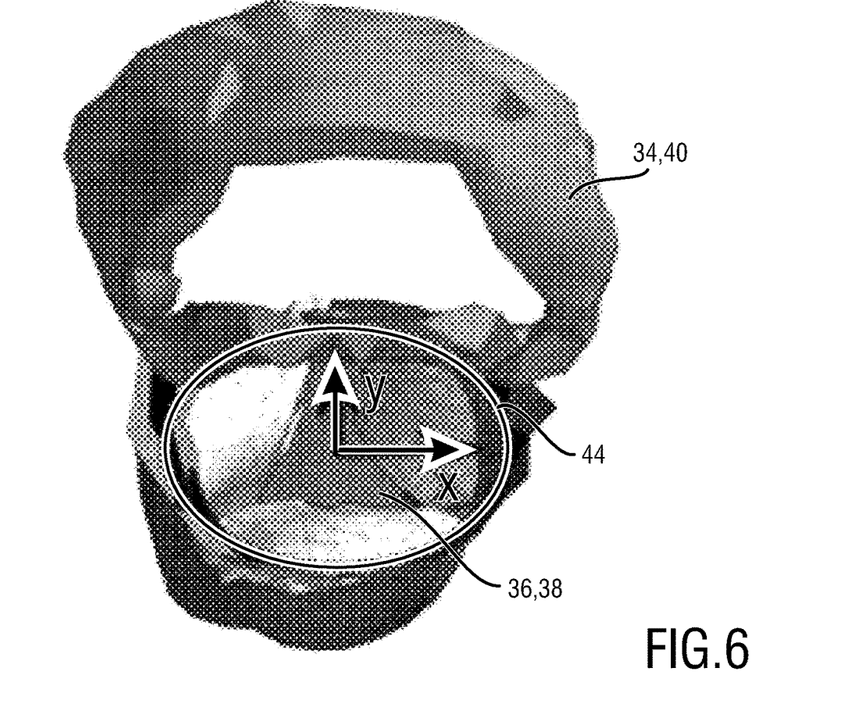
FIG. 6 shows the model of FIG. 5 from another side.

FIG. 3 shows a TEE ultrasound image from which it can be seen that the anterior mitral leaflet 34 in its open position at least partly extends into the left ventricular outflow tract 36 where the medical implant may be placed. In terms of the present invention, the left ventricular outflow tract 36 is therefore denoted as target implant region 38, and the anterior mitral valve leaflet 34 is denoted as locally adjacent region 40 that could interfere with the cardiac implant 42, as this is schematically illustrated in FIG. 4.

In the segmentation step, at least the target implant region 38 and the locally adjacent region 40 are segmented in a multi-step approach in order to determine the dynamics of the left ventricular outflow tract 36 and the anterior mitral leaflet 34. The model that is used thereto is represented as a triangular surface model with mean shape $\overline{m}$. First, the heart position is located using an adapted Generalized Hough Transform. Next, it is iteratively refined by determining the parameters of an affine transformation T that minimize the distance to detected boundaries (external energy $E_{ext}$). Finally, multiple iterations of a deformable adaptation are performed that is balanced between attraction to image boundaries ($E_{ext}$) and mean shape preservation ($E_{int}$). Details of such a boundary detection technique may be found in the scientific paper of Ecabert, O. et al. mentioned above, as well as in Peters, J. et al.: "Optimizing boundary detection via simulated search with applications to multi-modal heart segmentation", Medical Image Analysis 14(1) (2010) 70, which is herein incorporated by reference as well.

For the illustrated example of TAVI planning, it is sufficient to use a triangular surface model of the left heart that comprises endocardial surfaces of the left ventricle, the left atrium, the ascending aorta, and of the aortic and mitral valve.

The mean shape $\overline{m}$ contains two valves in half-open state. It is extended by two linear modes $\phi_m$ to model the valve dynamics, similar to PCA modes:

$$m(p_1,p_2) = \overline{m} + p_1\phi_1 + p_2\phi_2$$

However, these modes need not be calculated from PCA, but can be calculated as a linear interpolation between the open and closed state for each heart valve.

The coefficients $p_m$ describe the current state of each heart valve. For all vertices outside the respective valves, the vector elements of $\phi_m$ are zero and do thus not influence the shape of the remaining model.

The adaptation process is performed as follows: After the Generalized Hough Transform, the mean model with half-open valves is used to estimate a global rigid transformation T. At this step, no valve dynamics need to be estimated. Then, the coefficients $p_m$ are optimized during the deformable adaptation. The formulation of the shape constraining energy $E_{int}$ is given as:

$$E_{int} = \sum_{i=1}^{V} \sum_{j \in N(i)} ((v_i - v_j) - (T[m_i(p_1, p_2)] - T(m_j(p_1, p_2)]))^2$$

Here, V is the number of vertices in the model, N(i) are the neighbours of the ith vertex, $v_{i/j}$ are the vertex positions in the deformed mesh, and $m_{i/j}$ are the vertex positions in the model.

Furthermore, a penalty term can be added to the total energy with weight β to avoid unphysiological mode coefficients $p_m$.

To analyze data from a specific patient, all cardiac phases of the received image data set are segmented using the model and framework described above. To this end, the first cardiac phase is segmented, and the result is used as initialization for the next cardiac phase. Only the deformable adaptation is then performed for the succeeding cardiac phases with the respective previous results as initialization.

To compensate for global movement or other displacements, all meshes segmented from one time series are then preferably registered to the mesh at a endsystolic state. Most preferably, the aortic valve annulus points that are detected in each frame are registered onto each other to make all heart movement relative to the target implant region 38.

As a result of the above-mentioned segmentation, the movement trajectory of the region 40 (e.g. the anterior mitral leaflet 34) that is locally adjacent to the target implant region 38 (e.g. the left ventricular outflow tract 36) is determined for a plurality of different surface points. This allows to animate the movement of the anterior mitral leaflet 34 in a fairly accurate manner.

In order to simplify the movement analysis of the received trajectories, a coordinate system is preferably introduced by the segmentation unit 22. In the particular example of TAVI planning, this coordinate system is preferably arranged within the target implant region 38 (the left ventricular outflow tract 36), wherein the z-axis is arranged along the longitudinal axis along which the target implant region 38 substantially extends (see FIG. 5). The cross-section of the target implant region 38 may then be modelled as an elliptical ring 44, wherein the x-axis is aligned along the major axis of this ellipse 44 and the y-axis along the minor axis of the ellipse (see FIG. 6). The origin of this coordinate system may then be shifted along the z-axis to the aortic annulus plane 46. This way, all z-distances are referenced with respect to the aortic annulus plane 46.

3. Third Method Step S14 ("Implant Simulation")

In the implant simulation step that is performed by the simulation unit 24, the cardiac implant 42 and its position within the target implant region 38 is simulated. This is preferably done in each frame of the received 3D image sequence. The cardiac implant 42 may thereto be simulated by means of a virtual model having an elliptical cross-section, e.g. the cross-section of the target implant region 38 that has been determined within the segmentation unit 22. In the given example, the elliptical ring 44 determined within the segmentation step S12 may be extended along the z-axis along which the target implant region 38 substantially extends. Alternatively, other virtual 3D models of cardiac implants 42, which resemble the shape of a stent in a more realistic manner, may be used in the simulation. By means of the input interface 30, the user may also manually vary the size, the shape and/or the position of the simulated cardiac implant 42.

4. Fourth Method Step S16 ("Collision Detection")

In the collision detection step which is performed by the collision evaluation unit 26, an overlap of the simulated cardiac implant 42 with the segmented locally adjacent region 40 is calculated. In the given example it is calculated to what extent the anterior mitral leaflet 34 projects into the virtual cardiac implant 42. This calculated overlap is schematically illustrated in FIG. 4 and indicated by reference numeral 46. This is preferably done for each frame of the 3D image sequence.

The trajectories of several segmented points on the anterior mitral leaflet 34 may thereto be determined from the segmented, registered meshes (see segmentation step S12) with reference to the defined coordinate system. In the next step, the collision evaluation unit 26 preferably determines in each of the plurality of 3D cardiac images 14, 14' the overlap at a plurality of different spatial locations along the z-axis in order to receive the overlap information in each frame as a function of the longitudinal axis of the target implant region 38.

Furthermore, the collision evaluation unit 26 is configured to determine for each of the plurality of different spatial locations a maximum overlap 46 by comparing the overlaps 46 occurring in each frame of the 3D image sequence at the respective spatial locations with each other. This way, the extent of the maximum overlap at each position on the z-axis is determined. In order to facilitate the calculations, the collision evaluation unit 26 preferably only evaluates the maximum overlap for specific distinctive points on the z-axis (e.g. with a step size of 2.5 mm).

The above-mentioned collision calculation/evaluation may be performed by combining all segmented and registered points of the anterior mitral leaflet 34 that have been found in the segmentation S12 into a point cloud. The points of this point cloud may then be merged into groups according to the defined step size. For every group of points, the maximum overlap may then be calculated to receive the maximum overlap at the different positions on the z-axis.

5. Fifth Method Step S18 ("Feedback")

Finally, the feedback information concerning the calculated overlap 46 may be given out via the feedback unit 28. One example of such a feedback is shown in FIG. 7.

Figure 7:
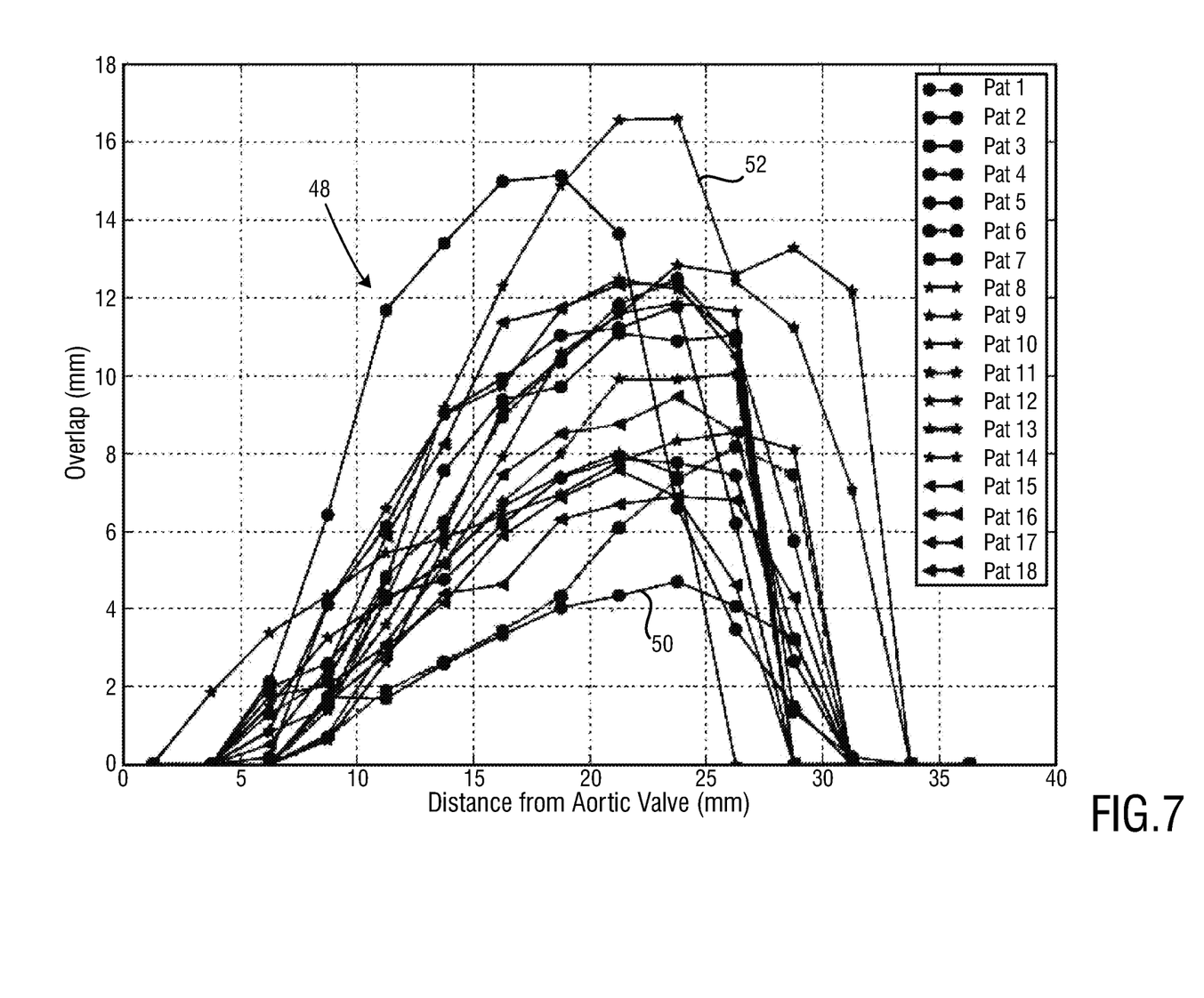
FIG. 7 illustrates different graphs that result from an overlap evaluation according to the present invention.

FIG. 7 shows a graphical representation 48 that illustrates the maximum overlaps 46 as a function of the different spatial locations along the z-axis. It is to be understood that these maximum overlap values are relative maxima, meaning the maximal overlap values that occur at the specific positions during a cardiac cycle. Each maximum overlap is received by evaluating the overlap at the respective position in each frame and comparing it to the values occurring at said position in the other frames.

The graphical representation 48 shows several overlap curves that have been determined from 3D TEE data sets of eighteen different patients. Each curve shows the maximum overlap between the mitral leaflet movement, and the virtual cardiac implant 42 as a function of the distance from the aortic annulus plane. Therefore, it can be seen that the absolute maximum overlap (point with largest overlap in each curve) varies considerably between patients, wherein not only the extent of the absolute maximum varies, but also the positions where the absolute maximum occurs. The patient with the smallest overlap (indicated by reference numeral 50) has an absolute maximum overlap of around 4.7 mm, whereas the patient with the largest overlap (indicated by reference numeral 52) has an absolute maximum overlap of around 16.6 mm. Also, the relative maximum overlap at a given implant depth varies considerably. At an implant depth of 12.5-15 mm, which is a typical depth for the lower rim of commercially available implants, the overlap varies between around 2.6 and 13.4 mm.

Figure 8A:
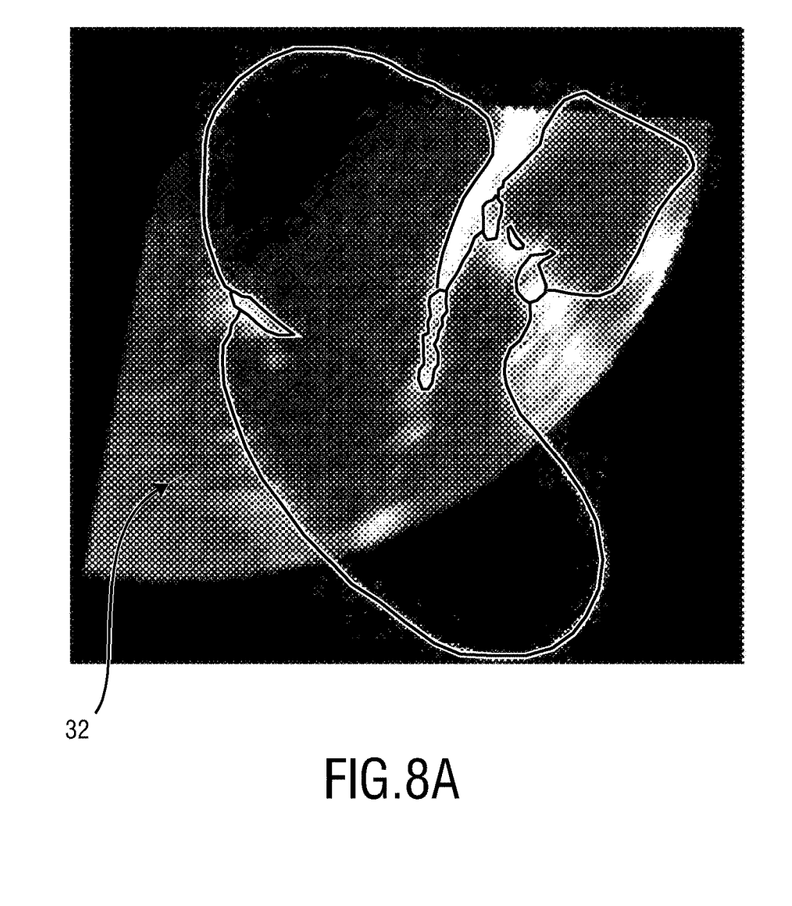
FIGS. 8A and 8B show further exemplary segmentations of cardiac images taken from two different patients.
Figure 8B:
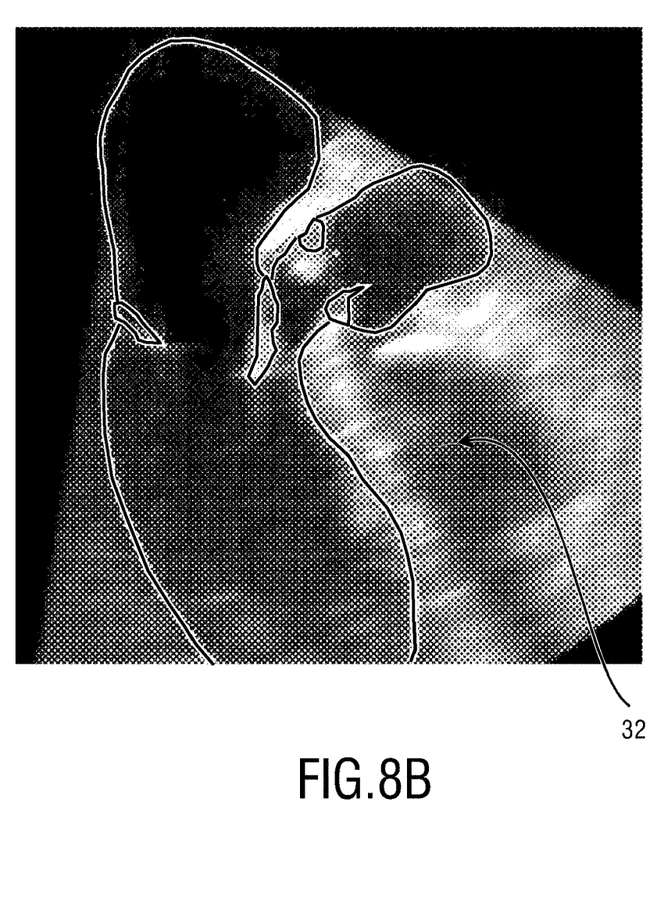

These individual differences may be also seen from the exemplary segmentations shown in FIGS. 8A and 8B. Both images show the heart of two different patients at a point in time during the cardiac cycle when the mitral valve is opened. By comparing the two images with each other, it can be seen that the overlap between the anterior mitral leaflet and the left ventricular outflow tract prolongation is quite different. In FIG. 8A, the overlap has an extent of around 8 mm, while the maximum overlap is located quite far from the aortic annulus plane. In FIG. 8B, the maximum overlap is over 15 mm and located a lot closer to the aortic annulus plane.

The given results show that the system and method according to the present invention is a powerful tool for planning an implantation of a cardiac implant. A graphical representation as given in FIG. 7 simplifies the risk evaluation a lot for the physician and also allows him to easily select the correctly shaped and sized cardiac implants.

In summary, the presented method allows to accurately plan an implantation of a cardiac implant, either in advance to or during the surgery. It allows to dynamically segment a series of medical 3D images and to calculate or estimate an overlap of the dynamical heart model with a virtual implant model. Even though the foregoing description has been mainly focused on TAVI, the presented method may also be used for planning other cardiac implants in other regions of the heart. It shall be also noted that the invention is not limited to a specific type of medical image (MR, CT, ultrasound), but may be implemented for various medical imaging techniques.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A medical imaging system for planning an implantation of an implant, comprising:
  a processor in communication with an interface, wherein the processor is programmed to:
    receive, via the interface, a plurality of three-dimensional (3D) images;
    segment within the plurality of 3D images a target implant region and a locally adjacent region that could interfere with the implant;
    simulate the implantation of the implant within the target implant region in at least two of the plurality of 3D images;
    evaluate an overlap of the simulated implant with the segmented locally adjacent region in at least two of the plurality of 3D images;
    determine overlap at a plurality of different spatial locations along an axis along which the target implant region substantially extends as a function of a depth of the implant; and
    provide feedback information, via a feedback unit, to a user indicative of the overlap evaluated.

2. The medical imaging system according to claim 1, wherein the processor is further programmed to;
  simulate the implantation of the implant within the target implant region in each of the plurality of 3D images; and
  evaluate the overlap of the simulated implant with the segmented locally adjacent region in each of the plurality of 3D images.

3. The medical imaging system according to claim 1, wherein the processor is further programmed to provide feedback information to the user indicative of the overlap evaluated in each of the plurality of 3D images.

4. The medical imaging system according to claim 1, wherein the processor is further programmed to provide feedback information including a quantified extent of the overlap and/or a location where the overlap occurs in the 3D images.

5. The medical imaging system according to claim 1, wherein the processor is further programmed to determine for each of the plurality of different spatial locations a maximum overlap by comparing the overlaps in the 3D images at the respective spatial locations with each other.

6. The medical imaging system according to claim 5, wherein the processor is further programmed to provide a graphical representation illustrating the maximum overlap as a function of the different spatial locations along the axis.

7. The medical imaging system according to claim 1, wherein the processor is further programmed to simulate the implant using a virtual model.

8. The medical imaging system according to claim 1, wherein the processor is further programmed to allow a user to vary one or more of a size, a shape, or a position of the simulated implant.

9. The medical imaging system according to claim 1, wherein the processor is further programmed to segment the target implant region and the locally adjacent region based on a model-based segmentation.

10. The medical imaging system according to claim 1, wherein the plurality of 3D images include 3D images acquired with an ultrasound imaging system.

11. The medical imaging system according to claim 1, wherein the processor is further configured to determine segmented trajectories for a plurality of different surface points.

12. The medical imaging system according to claim 1, wherein the overlap is determined at a plurality of spatial locations along the axis according to a defined step size.

13. A method for planning an implantation of an implant, comprising the steps of:
  receiving a plurality of three-dimensional (3D) images;
  segmenting within the plurality of 3D images a target implant region and a locally adjacent region that could interfere with the implant;
  simulating the implantation of the implant within the target implant region in at least two of the plurality of 3D images;
  evaluating an overlap of the simulated implant with the segmented locally adjacent region in at least two of the plurality of 3D images;
  determining for at least some of the plurality of 3D images an overlap along an axis along which the target implant region substantially extends as a function of a depth of the implant by comparing the overlaps in the 3D images with each other; and
  providing feedback information to a user concerning the evaluated overlap.

14. The method of claim 13, wherein the feedback information includes a quantified extent of the overlap and/or a location where the overlap occurs in the 3D images.

15. A computer program product comprising a non-transitory computer readable medium encoded with program code that when executed by a processor, enable the processor to:
  receive a plurality of three-dimensional (3D) images;
  segment within the plurality of 3D images a target implant region and a locally adjacent region that could interfere with an implant;
  simulate the implantation of the implant within the target implant region in at least two of the plurality of 3D images;
  evaluate an overlap of the simulated implant along an axis along which the implant substantially extends into the segmented locally adjacent region as a function of a depth of the implant in at least two of the plurality of 3D images; and
  provide feedback information to a user concerning the evaluated overlap.

16. The computer program product of claim 15, wherein the program code that when executed by the processor, further enables the processor to:

simulate the implantation of the implant within the target implant region in each of the plurality of 3D images; and evaluate the overlap of the simulated implant with the segmented locally adjacent region in each of the plurality of 3D images.

17. The computer program product of claim 15, wherein the program code that when executed by the processor, further enables the processor to determine for each of the plurality of different spatial locations a maximum overlap by comparing the overlaps in the 3D images at the respective spatial locations with each other.

18. The computer program product of claim 15, wherein the program code that when executed by the processor, further enables the processor to provide a graphical representation illustrating the maximum overlap as a function of the different spatial locations along the axis.

* * * * *